(12) United States Patent
Mignucci et al.

(10) Patent No.: US 8,968,325 B2
(45) Date of Patent: Mar. 3, 2015

(54) ANTERIOR SPINAL INTERBODY FUSION DELIVERY SYSTEM

(71) Applicant: Luis Antonio Mignucci, Plano, TX (US)

(72) Inventors: Luis Antonio Mignucci, Plano, TX (US); Javier E. Oliver, Plano, TX (US); Kenneth R. Konya, Lexington, TX (US); Willie A Janeka, Jr., Georgetown, TX (US)

(73) Assignee: Luis Antonio Mignucci, Plano, TX (US)

( * ) Notice: Subject to any disclaimer, the term of this patent is extended or adjusted under 35 U.S.C. 154(b) by 0 days.

(21) Appl. No.: 14/015,511

(22) Filed: Aug. 30, 2013

(65) Prior Publication Data

US 2014/0066941 A1 Mar. 6, 2014

Related U.S. Application Data

(63) Continuation-in-part of application No. 11/825,467, filed on Jul. 6, 2007, now Pat. No. 8,562,621.

(51) Int. Cl.
A61F 2/46 (2006.01)
A61F 2/30 (2006.01)
A61B 17/02 (2006.01)

(52) U.S. Cl.
CPC ............ *A61F 2/4611* (2013.01); *A61F 2/3094* (2013.01); *A61B 17/0206* (2013.01); *A61B 17/025* (2013.01); *A61F 2/4657* (2013.01); *A61B 2017/0256* (2013.01); *A61F 2002/4628* (2013.01); *A61F 2002/4687* (2013.01)
USPC ......................................................... 606/99

(58) Field of Classification Search
USPC .............................. 606/86 A, 90, 96, 99, 105; 623/17.11–17.16
See application file for complete search history.

(56) References Cited

U.S. PATENT DOCUMENTS

| | | | |
|---|---|---|---|
| 6,551,316 B1 | 4/2003 | Rinner et al. | |
| 6,616,671 B2 | 9/2003 | Landry et al. | |
| 6,648,895 B2 * | 11/2003 | Burkus et al. | 606/90 |
| 6,652,533 B2 | 11/2003 | O'Neil | |
| 6,712,825 B2 | 3/2004 | Aebi et al. | |
| 6,716,218 B2 | 4/2004 | Holmes et al. | |

(Continued)

FOREIGN PATENT DOCUMENTS

| | | |
|---|---|---|
| DE | 202005016360 | 2/2006 |
| WO | 03/099146 | 12/2003 |

(Continued)

OTHER PUBLICATIONS

International Search Report and the Written Opinion from PCT/US2008/083300, mailed May 11, 2008.

*Primary Examiner* — Christopher Beccia

(57) ABSTRACT

A surgical instrument is disclosed comprising a base having a tray, a first member and a second member. A first and second top arm are coupled near the proximal end of the base. At least one bottom finger is coupled to the distal end of the first member and at least one top finger is coupled to the distal end of the first top arm. At least a first lifting arm is located between the first member and the first top arm, said lifting arm comprising a cam for engaging the first top arm. Rotation of an adjustment member positioned near the proximal end of the first member engages at least one lifting arm. As the lifting arm moves towards the distal end of the first member, the cam engages and lifts the first top arm, displacing the first top finger to a separation distance from the bottom finger.

17 Claims, 13 Drawing Sheets

(56) References Cited

U.S. PATENT DOCUMENTS

| | | |
|---|---|---|
| 7,004,947 B2 | 2/2006 | Shluzas et al. |
| 7,081,118 B2 | 7/2006 | Weber et al. |
| 7,169,153 B2 | 1/2007 | Keller |
| 7,608,080 B2 | 10/2009 | Shipp et al. |
| 7,749,231 B2 | 7/2010 | Bonvallet et al. |
| 2003/0149438 A1 | 8/2003 | Nichols et al. |
| 2003/0225416 A1* | 12/2003 | Bonvallet et al. ............ 606/105 |
| 2005/0143747 A1* | 6/2005 | Zubok et al. .................. 606/90 |
| 2006/0036258 A1 | 2/2006 | Zucherman et al. |
| 2006/0074431 A1* | 4/2006 | Sutton et al. .................. 606/90 |
| 2007/0191856 A1* | 8/2007 | Gil et al. ........................ 606/90 |

FOREIGN PATENT DOCUMENTS

| | | |
|---|---|---|
| WO | 2007/018457 | 2/2007 |
| WO | 2008/073185 | 6/2008 |

\* cited by examiner

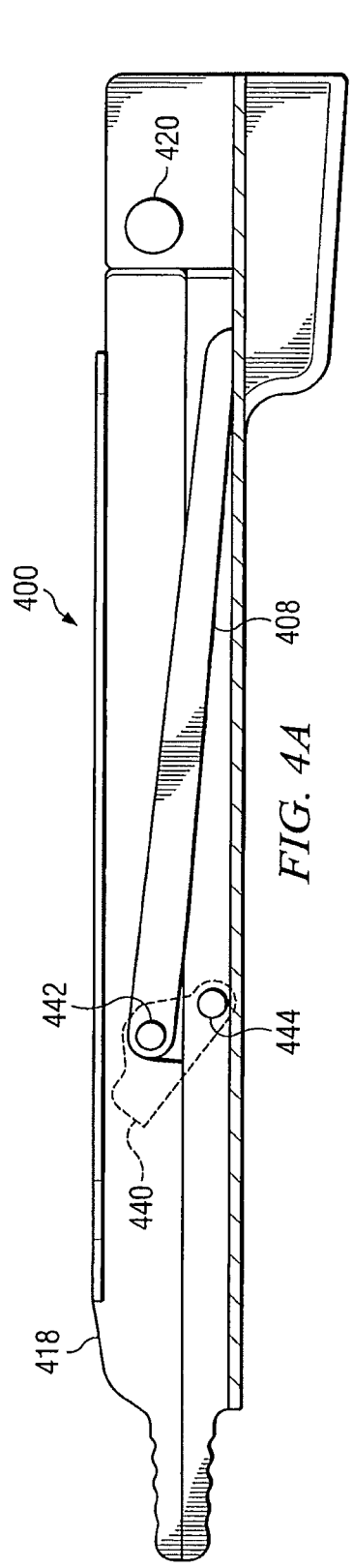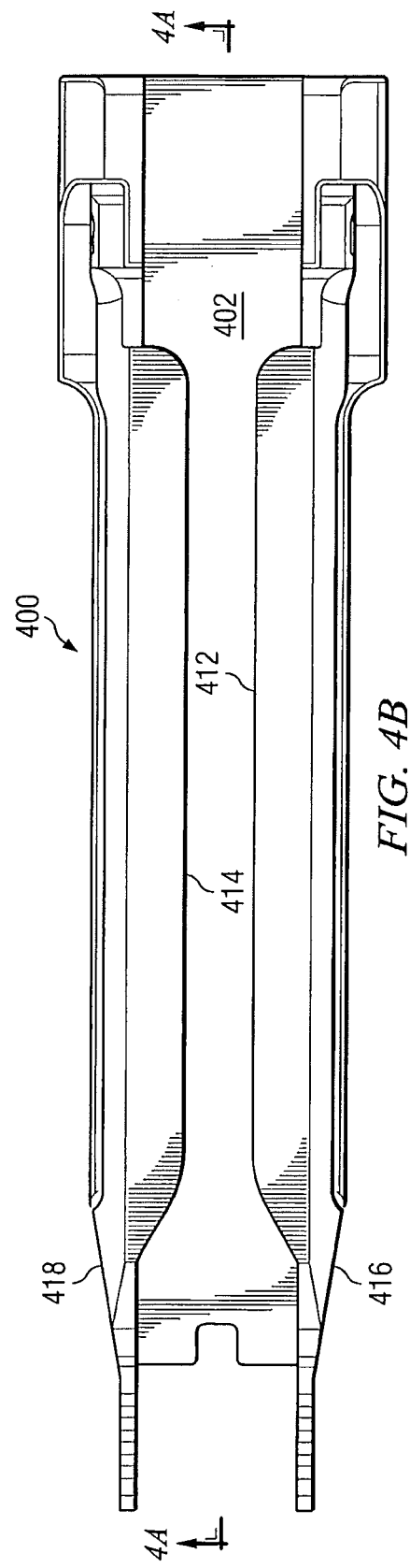
FIG. 4A
FIG. 4B

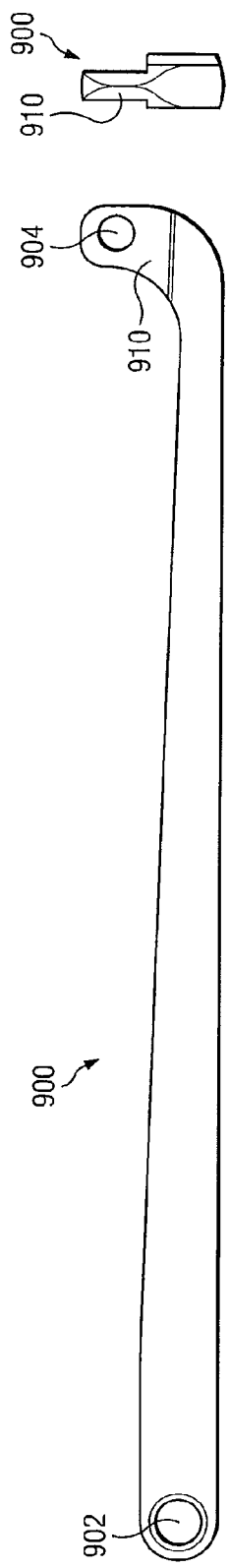
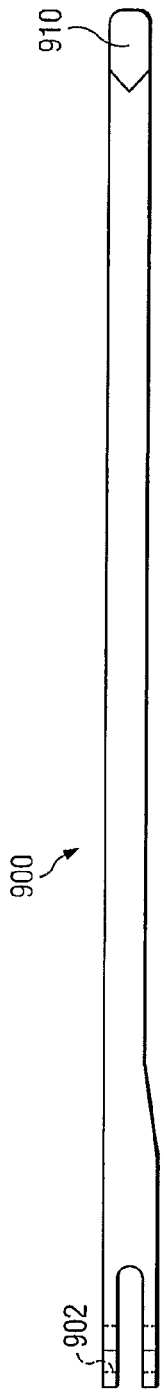
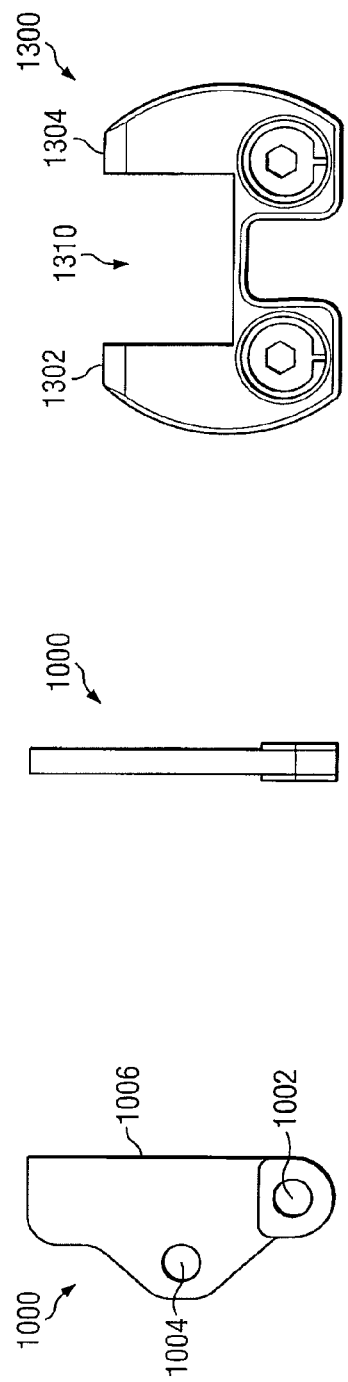
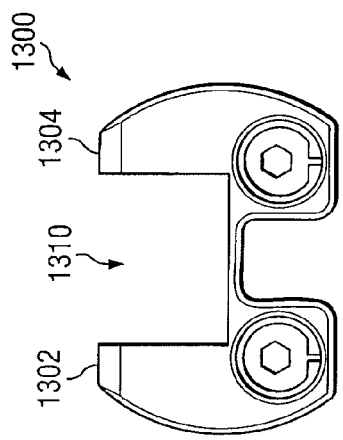
FIG. 9A
FIG. 9B
FIG. 9C
FIG. 10A
FIG. 10B
FIG. 13C

SECTION A-A

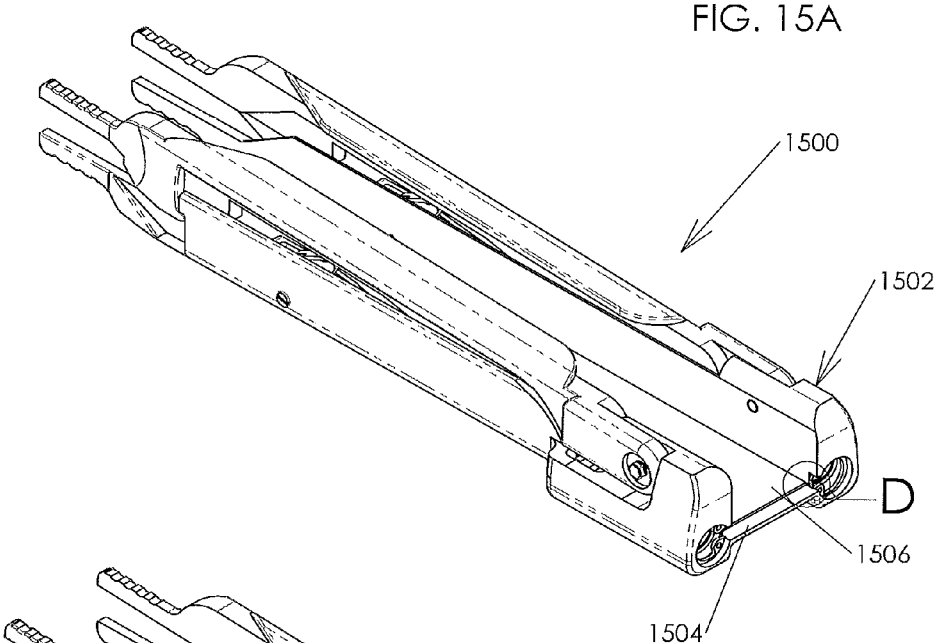
FIG. 15A
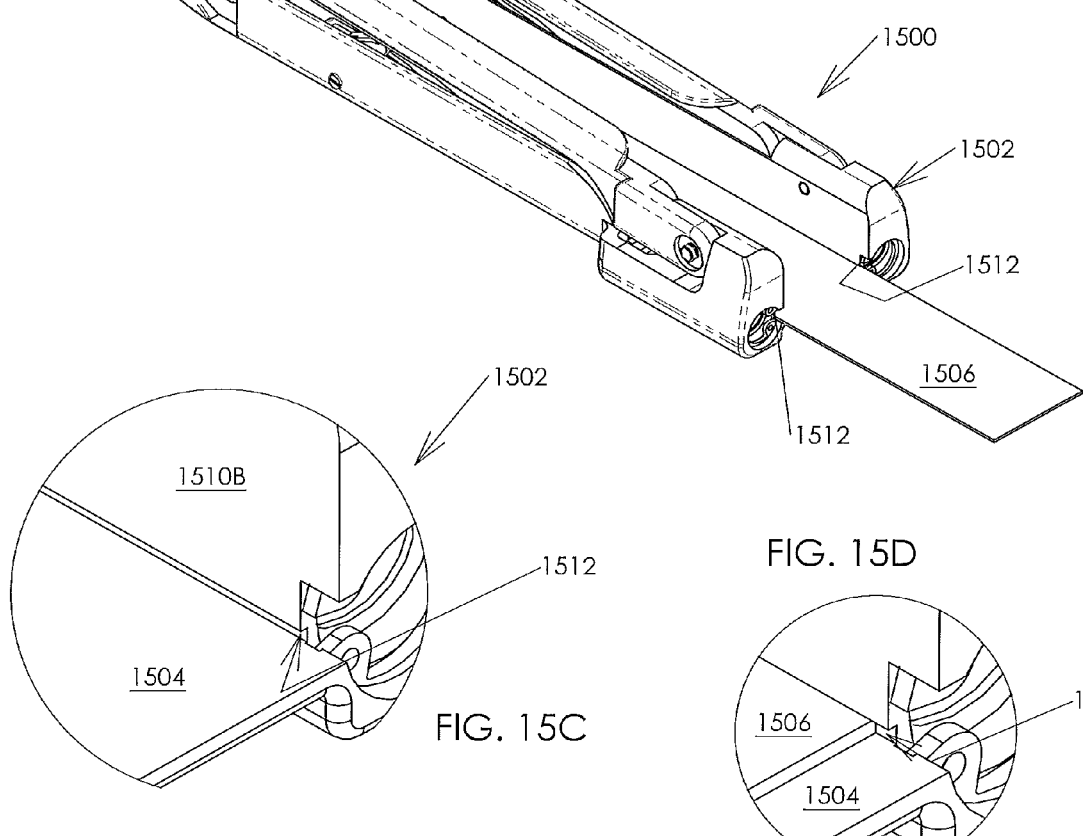
FIG. 15B
FIG. 15C
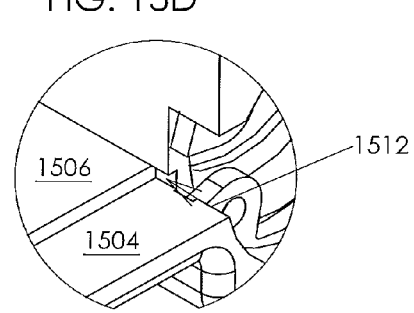
FIG. 15D

ANTERIOR SPINAL INTERBODY FUSION DELIVERY SYSTEM

CROSS-REFERENCE TO RELATED APPLICATION

This application is a Continuation-in-Part Application of and claims priority to application Ser. No. 11/825,467, filed Jul. 7, 2007, entitled "Anterior Spinal Interbody Fusion Delivery System," the entire contents of which are incorporated herein by reference.

FIELD OF THE INVENTION

The present disclosure relates generally to surgical instruments, and more specifically, an embodiment of a spinal distraction and graft delivery system, and methods of using said system.

BACKGROUND

Intravertebral discs, which separate and cushion the individual vertebrae of the human spine from each other, allow for the flexibility of the spine while still providing structural support. The intravertebral discs are often subject to degeneration with age, resulting in herniations, displacements, or other dysfunctions, thereby causing severe pain and lowering the quality of life. Artificial disc surgery, one preferred method of addressing this problem, involves the removal of the damaged disc and replacing it with an implant. This requires a surgical procedure in which the vertebrae adjacent to the damaged disc are separated (distracted), the damaged disc is removed, and an implant is positioned into the space between the distracted device.

Prior art spinal distraction instruments and spinal implant insertion instruments are known to those skilled in the art. For instance, a conventional spinal distraction device typically consists of two first class levers, hinged together to provide a spreading force at the distal end placed between the vertebrae when a spreading force is applied at the proximal end. Such a distraction device functions similarly to a pair of pliers.

A problem with this technology has been the danger of damaging surrounding soft tissues, especially the vulnerable nerve roots, during the distraction and implantation procedure. Therefore, what is required is solution that protects the soft tissue from being pinched or damaged.

Another problem with this technology has been that a clear passageway for the implantable procedure is not defined. Therefore, what is also required is a solution that provides for a clear implantation path while the vertebrae remain in a distracted position without significant obstruction of the working space. This also allows for a much shorter surgical procedure due to a more efficient means of implantation.

One unsatisfactory approach, in an attempt to solve the above-discussed problems is shown in FIGS. 1A and 1B, which shows a conventional distraction and implantation surgical device 100. Device 100 consists of two arms 102 and 104, each ending in a pair of fingers, 106, and 108, respectively. The fingers are inserted between two vertebrae, and distraction occurs by applying squeezing pressure between the lower arm 104 and a third arm 110 shown in FIG. 1B. The force is transferred to the upper arm through projection 112, resulting in the separation of fingers 106 and 108, and in turn the distraction of the spine. However, a disadvantage of this approach is that it does not adequately protect the soft tissues from damage.

Another disadvantage of the conventional instrument shown in FIGS. 1A-1B is the inability to finely tune the distraction distance and to adjust for spinal curvature during the distraction of the vertebrae. Therefore, what is also needed is a solution that addresses these needed functions.

Heretofore, the requirements of protecting the soft tissues from damage during distraction of the vertebrae and the implantation of a graft, providing a clear implantation path, and providing a finely tunable distraction that is able to adjust for spinal curvature referred to above have not been fully met in a surgical instrument. What is needed is a solution that simultaneously solves all of these problems.

SUMMARY

The present disclosure provides, in one embodiment, a surgical instrument comprising a base having a tray, a first member and a second member, said base, tray, first member and second member each comprising a proximal and distal end and wherein said tray, first member, and second member define a passageway; a first top arm coupled near the proximal end of the base; a second top arm coupled near the proximal end of the base; at least one bottom finger coupled to the distal end of the first member; at least one top finger coupled to the distal end of the first top arm; at least a first lifting arm located between the first member and the first top arm, said lifting arm comprising a cam for engaging the first top arm; and at least one adjustment member positioned near the proximal end of the first member, wherein rotation of said adjustment member engages a proximal end of the at least one lifting arm for moving said lifting arm between said first member and first top arm; wherein as the lifting arm moves towards the distal end of the first member, the cam engages and lifts the first top arm thereby displacing the first top finger to a separation distance from the bottom finger.

In another embodiment, a surgical instrument further comprises a second top finger coupled to the distal end of the second top arm; a second lifting arm located between the second member and the second top arm, said second lifting arm comprising a cam for engaging the second top arm; and a second adjustment member positioned near the proximal end of the second member, wherein rotation of said second adjustment member engages a proximal end of the second lifting arm for moving said second lifting arm between the second member and second top arm; wherein as the second lifting arm moves towards the distal end of the second member, the cam engages and lifts the second top arm thereby displacing the second top finger to a separation distance from the second bottom finger.

In some embodiments the surgical device may further comprise a second bottom finger coupled to the distal end of the second member; a second top finger coupled to the distal end of the second top arm; a second lifting arm located between the second member and the second top arm, said second lifting arm comprising a cam for engaging the second top arm; and a second adjustment member positioned near the proximal end of the second member, wherein rotation of said second adjustment member engages a proximal end of the second lifting arm for moving said second lifting arm between the second member and second top arm; wherein as the second lifting arm moves towards the distal end of the second member, the cam engages and lifts the second top arm thereby displacing the second top finger to a separation distance from the second bottom finger.

Yet in another embodiment of the present disclosure, a method for manufacturing a surgical instrument comprises providing a base having a tray, a first member and a second member, said base, tray, first member and second member each comprising a proximal and distal end and wherein said tray, first member, and second member define a passageway; providing a first top arm and coupling said first top arm near the proximal end of the base; providing a second top arm and coupling said second top arm near the proximal end of the base; providing at least one bottom finger and coupling said one bottom finger to the distal end of the first member; providing at least one top finger and coupling said one top finger to the distal end of the first top arm; providing at least a first lifting arm located between the first member and the first top arm, said lifting arm comprising a cam for engaging the first top arm; and providing at least one adjustment member, said adjustment member positioned near the proximal end of the first member, wherein rotation of said adjustment member engages a proximal end of the at least one lifting arm for moving said lifting arm between said first member and first top arm.

In some embodiments, the method may further comprise providing a second bottom finger and coupling said second bottom finger to the distal end of the second member; providing a second top finger, and coupling said second top finger to the distal end of the second top arm; providing a second lifting arm located between the second member and the second top arm, said second lifting arm comprising a cam for engaging the second top arm; and providing a second adjustment member positioned near the proximal end of the second member, wherein rotation of said second adjustment member engages a proximal end of the second lifting arm for moving said second lifting arm between the second member and second top arm.

BRIEF DESCRIPTION OF THE DRAWINGS

For a more complete understanding of the disclosure, reference is now made to the following descriptions taken in conjunction with the accompanying drawing, in which:

FIGS. 4A-4E show various views of the surgical device shown in FIGS. 2A and 2B according to the present disclosure;

FIGS. 9A-9C show various views of one embodiment of a draw arm according to the present disclosure;

FIGS. 10A-10B show two views of one embodiment of a lift arm according to the present disclosure;

FIGS. 13A-13C shows several views of yet another embodiment according to the present disclosure;

FIG. 15A is perspective view of yet another embodiment of a surgical instrument according to the present disclosure;

FIG. 15B is another view of the embodiment shown in FIG. 15A;

FIG. 15C is another view of the embodiment shown in FIG. 15A; and

FIG. 15D is yet another view of the embodiment shown in FIG. 15A.

DETAILED DESCRIPTION

Embodiments of the present disclosure and the various features and advantageous details thereof are explained more fully with reference to the non-limiting embodiments that are illustrated in the accompanying drawings and detailed in the following description. The detailed description and the specific examples, while indicating certain embodiments of the present disclosure, are given by way of illustration and not by way of limitation.

In general, the present disclosure is relates to a surgical instrument. The surgical instrument of the present disclosure provides an anterior spinal interbody fusion (ASIF) delivery system. The surgical instrument enables clear access between vertebrae for the insertion of implantable grafts. The access is provided by inserting pairs of displaceable fingers between vertebrae and distracting the vertebrae by displacing the fingers through a rotational force applied at the proximal end of the instrument. The instrument includes a clear passageway to the distracted space which provides access to the intravertebral space for the removal of a damaged disc, preparation of the disc space and the insertion of a graft. The implantable graft may be, for example, a femur graft (irregular disc shaped), a cylindrical graft, or a conical graft. The shape and surfaces of the graft tray are designed to protect the surrounding tissues, such as the vulnerable nerve roots, from being pinched or otherwise damaged while providing such a clear passageway. The instrument may be used for operation on either the cervical, thoracic, or lumbar sections of the human spine.

Figure 2A:
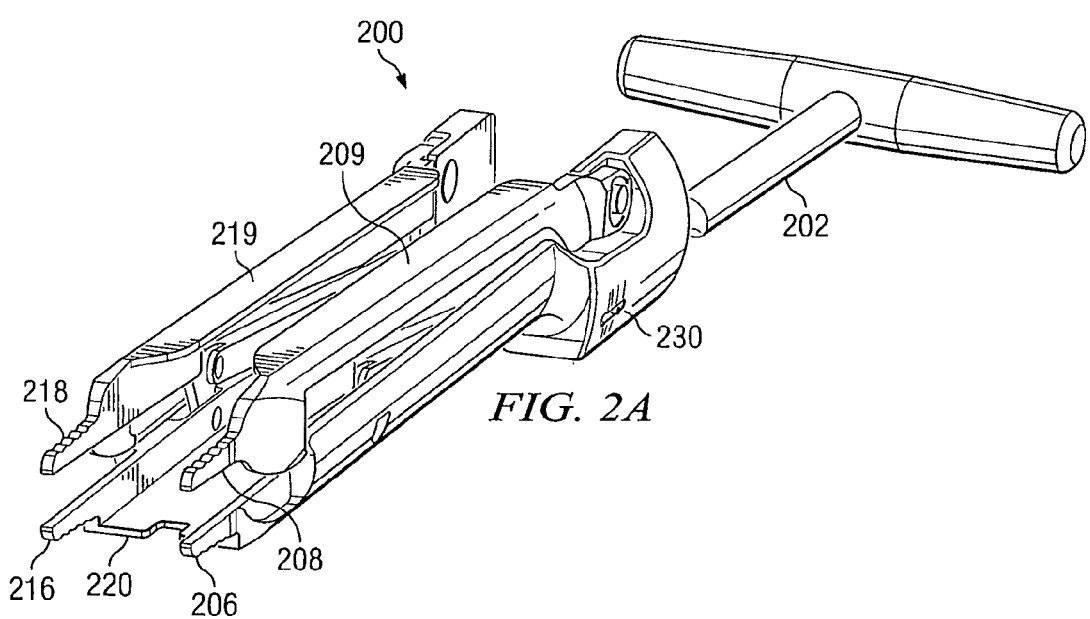
FIGS. 2A and 2B show two views of one embodiment of surgical device according to the present disclosure.
Figure 2B:
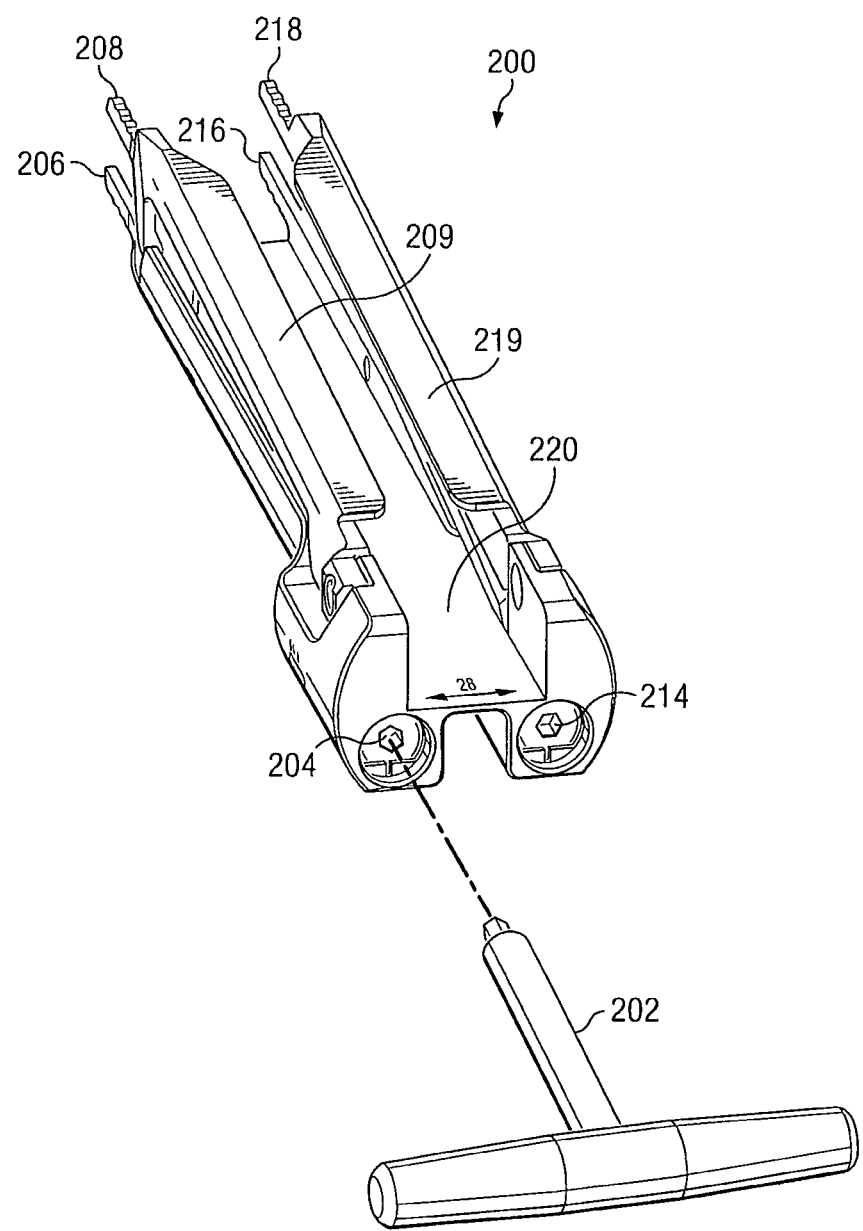

FIGS. 2A and 2B show two perspective views of one embodiment of a surgical instrument 200 according to the present disclosure. The instrument 200 is operated with a hex drive 202, which is mated to fit inside two hex-keyed pull nuts, left pull nut 204 and right pull nut 214 (shown in FIG. 2B), located at the proximal end of the instrument 200. Two pairs of serrated fingers are located at the distal end of the device. The serrations provide stability of the instrument in place during surgery. The first pair of fingers, left stationary finger 206, and right stationary finger 216, are stationary with respect to the tray (sometimes called the base) 220 of the instrument. The adjustable left finger 208 is coupled to the adjustable left top arm 209, and adjustable right finger 218 is coupled to the adjustable right top arm 219. The two top arms 209 and 219 are each displaceable with relation to the base 220. Rotation of the left pull nut 204 by turning the hex drive 202 leads to the displacement of the left top arm 209, which leads to the separation of the left adjustable finger 208 from the left stationary finger 206. Likewise, rotation of the right pull nut 214 by turning the hex drive 202 leads to the displacement of the right top arm 219, which leads to the separation of the right adjustable finger 218 from the right stationary finger 216.

The overall outside shape of the instrument is cylindrical, with a tapered entry end. This shape is for ease of use, ergonomic shape that fits well into the hand and prevents any tearing of the surgeon's glove. The tapered end minimizes the size of the incision and helps to bypass all the internal nerves, blood vessels, and other soft tissues sensitive to damage. In addition, smooth side walls and the internally contained distracting mechanism further helps to protect vulnerable surrounding soft structures during the surgical procedure. The smooth sliding surface inside the access passageway allows for different forms, sizes, and materials to be implanted with ease into the intravertebral disc space.

Figure 3:
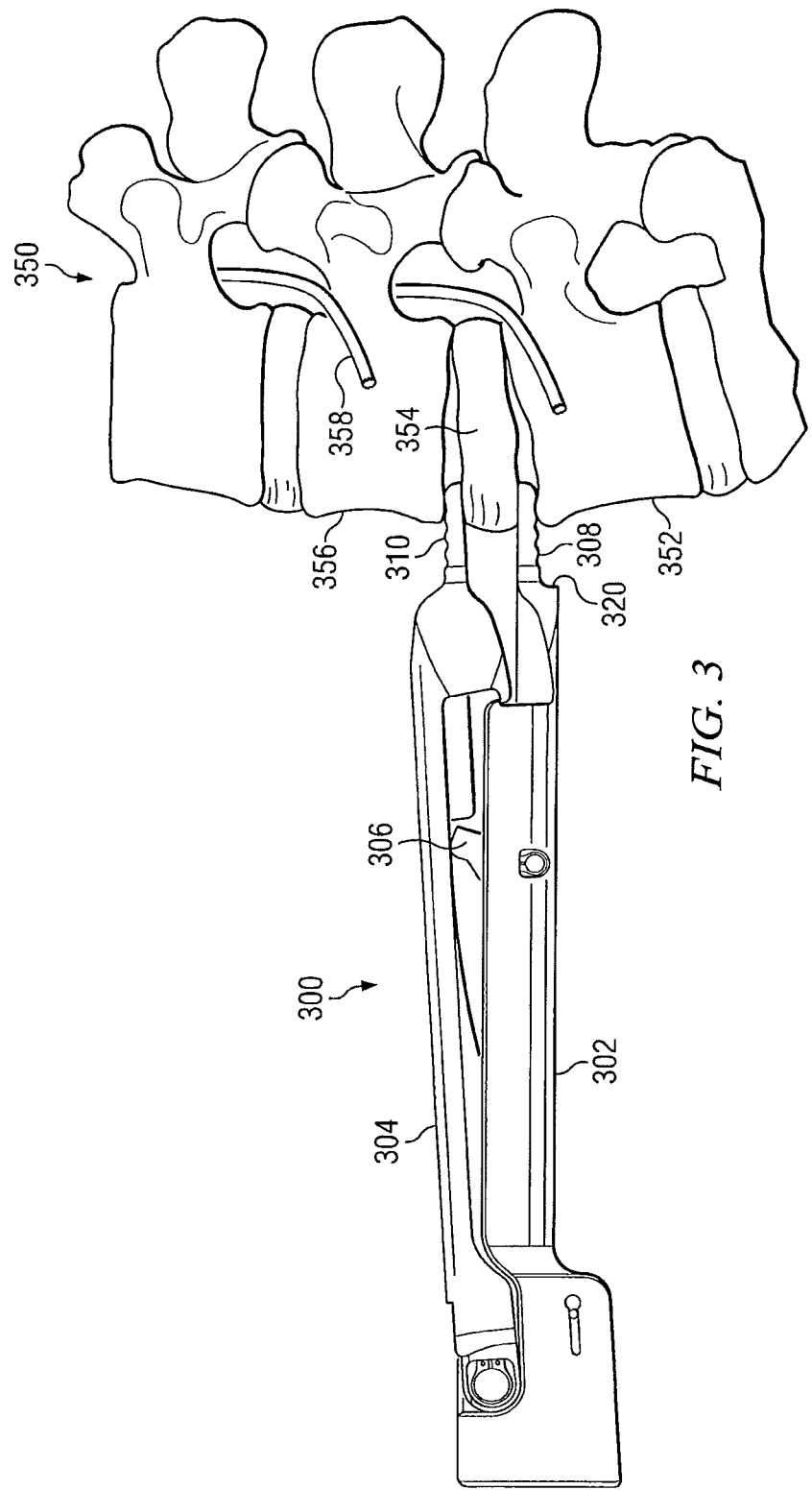
FIG. 3 illustrates one embodiment of a method of using one embodiment of surgical device according to the present disclosure.

FIG. 3 shows one embodiment of using an instrument according to the present disclosure. The instrument 300 is positioned anteriorly to the spine 350. Stationary fingers 308 and movable fingers are inserted between vertebra 352 and 356. Vertebra 352 may be, for example, L5 (the fifth lumbar vertebra), and vertebra 356 may be L4 (the fourth lumbar vertebra). By using the hex drive to turn the left and right pull nuts (not shown in FIG. 3), the left and right top arms 304 are lifted from the tray 302 by the left and right lift arms 306. This separates the fingers 308 and 310 and distracts vertebra 352 and 356 from each other, without damaging any nerve roots 358. The distraction distances of the left and right movable fingers are independently adjusted. After distracting the vertebrae, the damaged disc is removed by the surgeon from in-between the distracted vertebrae. The damaged disc may be removed through an access area located at the bottom front 320 of the graft tray. To facilitate the removal of the damaged disc, the bottom of the graft tray is located below the contact area of the stationary (bottom) fingers. Subsequently to the removal of the old disc and preparation of the intravertebral space, an implantable graft 354 is placed between the vertebrae, through the clear passageway provided by the tray 302, using, for example, thin forceps (not shown).

Figure 1A:
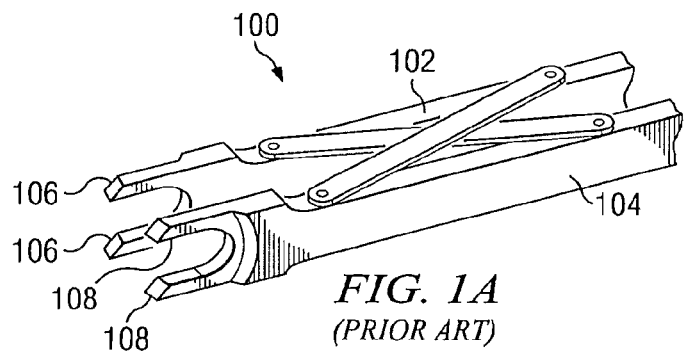
FIGS. 1A and 1B show two views of a conventional spinal distraction device.
Figure 1B:
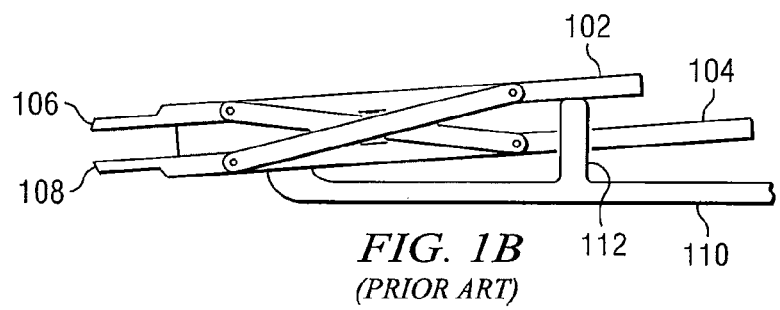

One of the features of the present disclosure is the ability to individually control the separation of the left pair of fingers 206 and 208 and the right pair of fingers 216 and 208. Conventional distraction instruments such as the one shown in FIGS. 1A and 1B lack this feature. Thus, the separation distance of the left pair of fingers 206 and 208 can be different from the separation distance of the right pair of fingers 216 and 218, and can vary over the whole range of distances available. For example, the left pair of fingers can be completely closed while the right pair of fingers remains completely open. This feature of the present disclosure is essential, for example, when using the instrument 200 on a spine with a significant side bend. The ability to separately control the distraction distance of the left and right side is also useful in the implantation of irregularly shaped implantable grafts. The narrow serrated strong finger tips insert into the disc space and maximally distract the spine without significant obstruction of the working space for the surgeon. In addition, this device has a 470 measuring scale on both sides that is used to provide the surgeon the distraction opening for each independent pair of fingers.

Another feature of the present disclosure is the ability to finely tune the separation distance of the fingers through the use of the rotational hex drive. An optional measurement device 230 is shown in FIG. 2A, which measures the separation distance of the left pair of fingers. An identical measurement device (not shown) is located on the right side of the instrument. This allows the surgeon to achieve a desired distraction distance on each side. Such a desired distraction distance can be determined diagnostically before surgery.

In addition, it is easy for the surgeon to insert and turn the ergonomically designed hex drive and separate the fingers. The hex drive is removed after the desired separation distance is achieved. This makes the instrument easy to use during surgery and does not create unnecessary obstructions for the path of the implantation graft. The heavy and well balanced instrument frame combined with the serrated fingers allows the instrument to lock into place, and frees the assistant's and the surgeon's hands for other tasks. The instrument is easy to remove from the intravertebral space at the end of the procedure due to the easily collapsible fingers, by simply reversing the rotation of the pull nuts with the hex drive.

The mechanism by which the pull nut activates and elevates the top arm 209 from the base 220 will now be described. The pull nut 204 has internal threads rotating freely in the instrument frame bore, threading onto a pull pin. The pull nut rotates in a stationary position during activation. The pull pin has external threads on one end and a through-slot on the other end to accommodate a draw arm, and the pull pin traverses along the axis of the pull nut during activation. The draw arm pivots in the pull pin at one end, and attaches to a lift arm at the other end. The draw arm is pulled along the axis of the pull pin as the pull pin traverses along the axis of the pull nut. The lift arm pivots in a fixed position on one end, being attached to the instrument frame. The other end of the lift arm makes contact with the underside of the top arm through a radial surface. The draw arm attaches midway to the lift arm, forcing the lift arm to rotate during activation while the draw arm is being pulled. The rotation of the lift arm forces the top arm to elevate from the base, thus separating the stationary and movable fingers. The pull pin, the draw arm, and the lift arm are not clearly visible in FIGS. 2A and 2B, but will be described in detail below with reference to the appropriate figures.

Figure 4C:
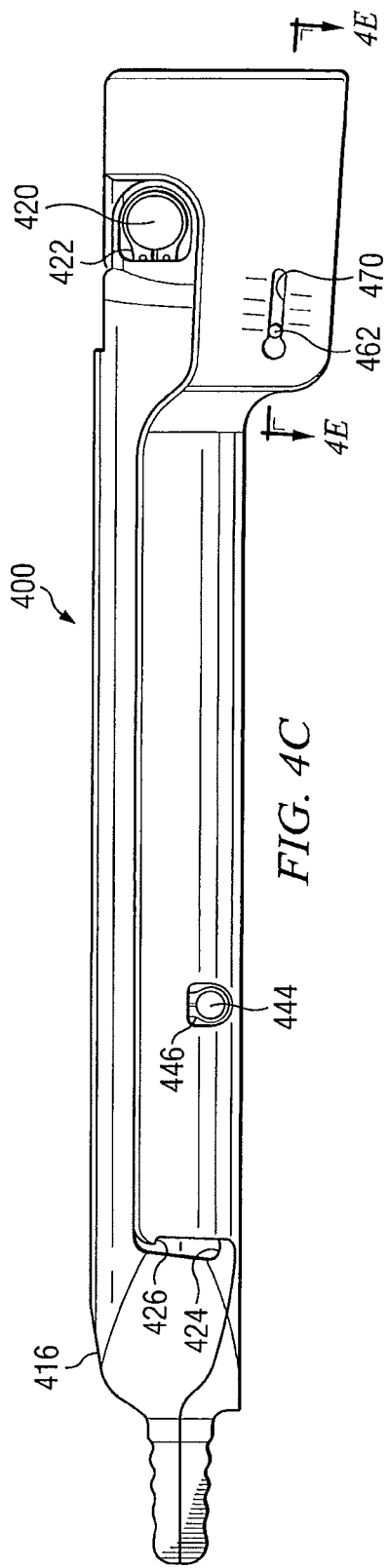
Figure 4E:
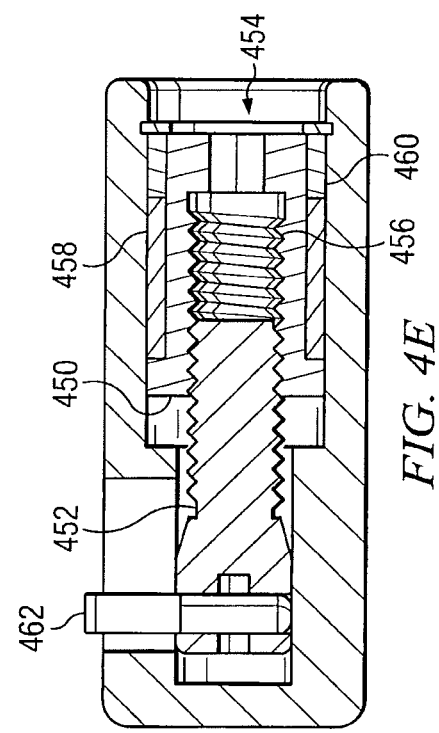
Figure 4D:
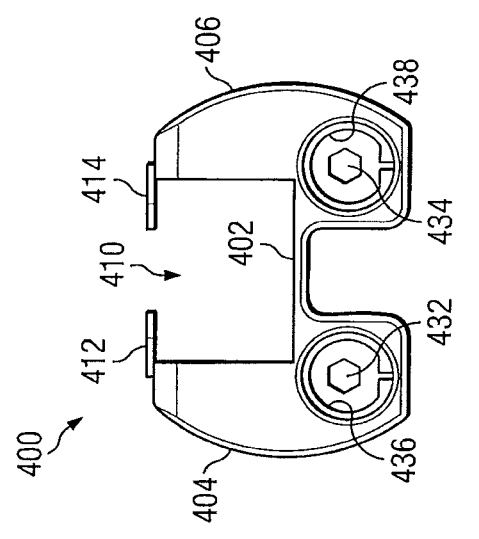

FIGS. 4A-4E show various views of the complete instrument. FIG. 4B shows the top view of the complete instrument. FIG. 4A shows the sectional view along section A-A of FIG. 4B. FIG. 4C shows the side view of the instrument, and FIG. 4D shows the end view of the instrument. Finally, FIG. 4E is the sectional view along section B-B of FIG. 4C.

The main frame, sometimes called the tray of the instrument 400, as shown in the end view of FIG. 4D, consists of the base 402, the left side wall 404, and the right side wall 406. Together, the base, the left side wall, and the right side wall, define a clear access path 410 for the implantable graft, the top of which has a longitudinal place window for monitoring the path of the graft. The upper boundary of the access path is defined by the left flange 412 of the left top arm 416, and the right flange 414 of the right top arm 418 (as shown in FIG. 4A). The partial covering of the top of this access path protects the access path from any intervening tissues, while providing a longitudinal place window which allows visual inspection of the path of the graft through the access path. FIG. 4D also shows the left pull nut 432 and right pull nut 434, which are held in place with left snap ring 436 and washer (not shown), and the right snap ring 438 and washer (not shown). In some embodiments, the pull nut may be threaded and secured in place without requiring a snap ring and washer.

As can be seen in FIG. 4C, the top arm 416 is coupled to the instrument frame 400 through a pivot pin 420, around which the top arm is free to rotate. The pivot pin is secured with a snap ring 422 and a washer (not shown). The top arm has a lip 424, which engages a similar lip 426 of the left side wall of the frame 400, once the top arm is lifted past a certain height. This sets the maximum height to which the top arm can be lifted and prevent damage to the human spine from excessive distraction.

FIG. 4A shows the right draw arm in position. The right draw arm is attached to the right pull pin through a step pin (see FIG. 9B). The other end of the right draw arm is coupled to the right lift arm 440 through a right pivot pin 442. The right lift arm 440 is shown with a dotted line in FIG. 4A, because it is covered by the sides of the right top arm 418. The right lift arm is coupled to the instrument frame 400 through a right lift pin 444, which is secured with an external snap ring 446 (shown in FIG. 4C). When the pull pin pulls the draw arm proximally, the draw arm pulls on the lift arm through the pivot pin, which causes the lift arm to rotate around the lift pin and in turn lift the top arm. The left top arm, left draw arm, and left lift arm are coupled in the same manner.

Figure 5:
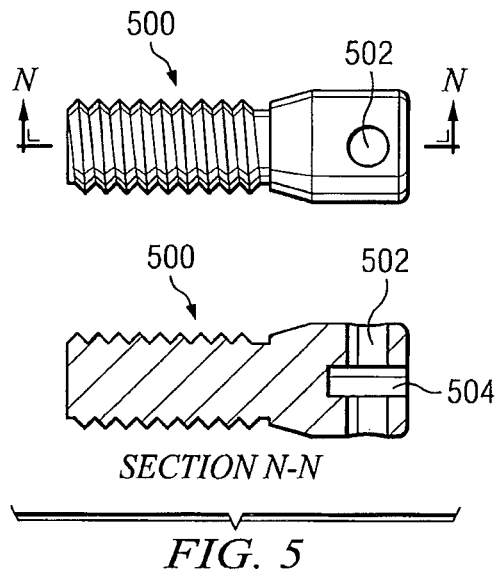
FIG. 5 shows one embodiment of a pull pin according to the present disclosure.
Figure 7:
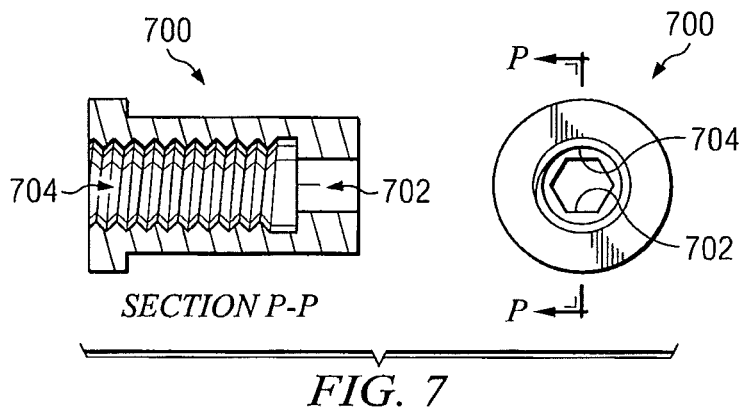
FIG. 7 shows one embodiment of a pull nut according to the present disclosure.

FIG. 4E shows the details of section B-B of FIG. 4C, illustrating the pull nut 450 and the pull pin 452. In this case, the left pull nut and left pull pin are shown. The right pull nut and pull pin are coupled in the same manner. Details of the pull nut are shown in FIG. 5 and details of the pull pin are shown in FIG. 7. Applying the hex drive to the mated hex-keyed opening 454 causes the pull nut 450 to rotate. The internal threads 456 of the pull nut are mated with the external threads of the pull pin 452. The rotation of the pull nut causes the pull pin to traverse along its axis. The pull nut is coupled to a sleeve 458 to allow for smooth rotation in the instrument frame, and a stop sleeve 460, which prevent the pull nut from rotating past a maximum set distance. A step pin 462 is shown coupled to the pull pin 452. The step pin serves to couple the draw arm to the pull pin. The step pin also serves as a measuring device by extending to the outside of the instrument frame and slides in a groove 470 (shown in FIG. 4C) in the instrument frame, which is marked with numbers. The measuring device, sometimes called the distraction gauge, indicates the separation distance of the fingers.

Pull pin 500 is shown in FIG. 5. The pull pin has a hole 502 transversely to its axis for accommodating the step pin. Slot 504 along the axis of the pull pin accommodates the draw arm, which secures the step pin into place.

Figure 6:
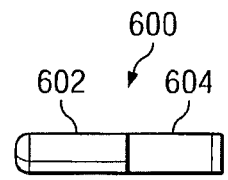
FIG. 6 shows one embodiment of a step pin according to the present disclosure.
Figure 6:
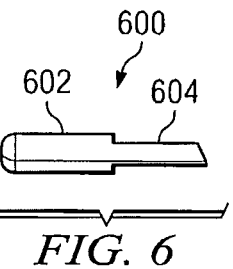

Step pin 600 is shown in FIG. 6. The thicker section 602 of the step pin secures the draw arm to the pull pin and allows the draw arm to rotate around the step pin. The thin section of the pull pin 604 extends to the outside of the measurement frame and slides in a groove (item 470 in FIG. 4C) marked with numbers, which indicate the separation distance of the fingers.

Pull nut 700 is shown in FIG. 7. The hex-shape opening 702 is formed to accommodate a hex drive wrench. The hollow core 704 of the pull nut is lined with internal threads which match the external threads of the pull pin.

Figure 8A:
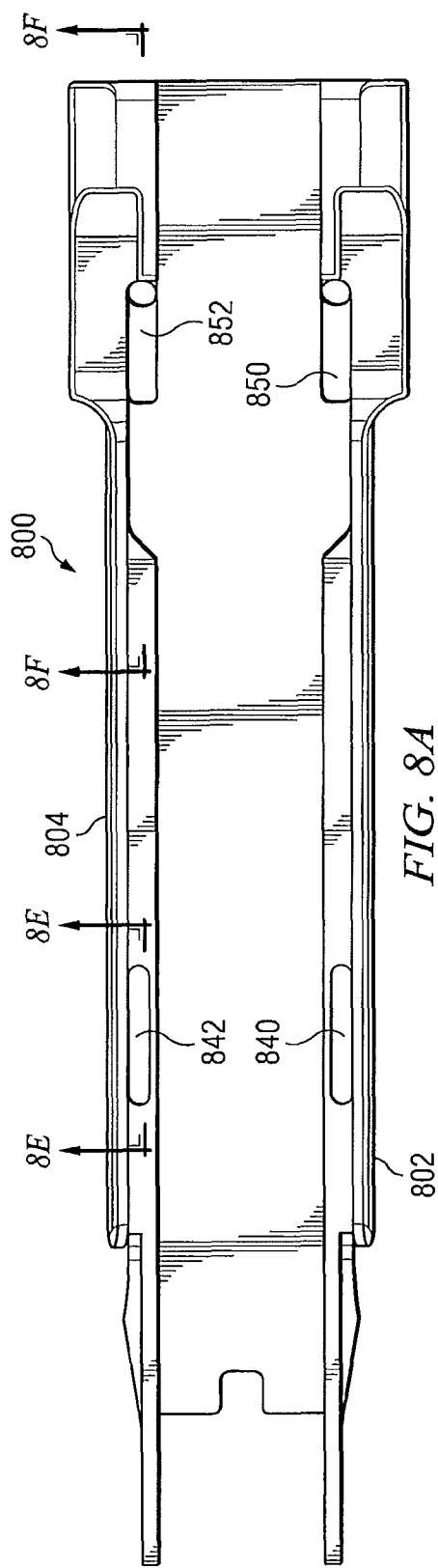
FIGS. 8A-8F show various views of one embodiment of a tray according to the present disclosure.
Figure 8B:
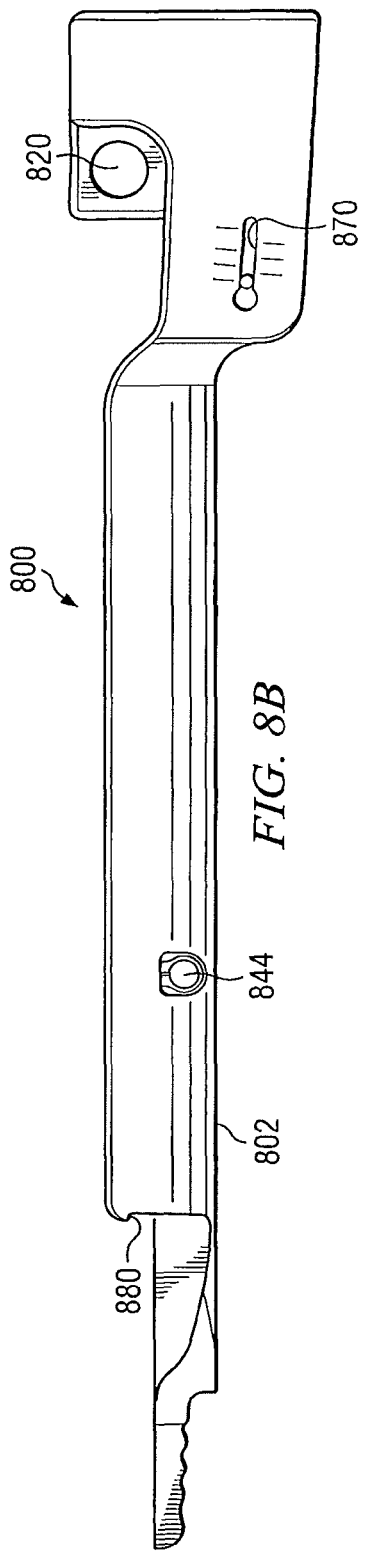
Figure 8C:
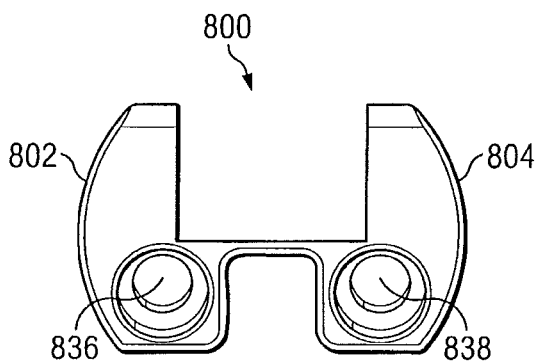
Figure 8D:
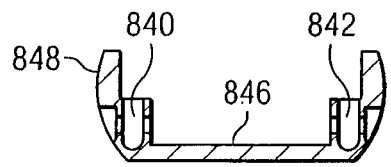
Figure 8E:
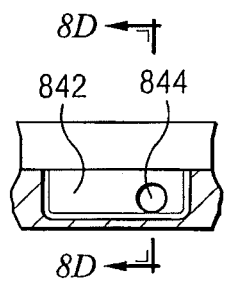

FIGS. 8A-8F show the instrument tray, sometimes called the instrument frame, without the top arms, lift arms, or draw arms. FIG. 8A shows the top view of the tray 800. FIG. 8B shows the side view of tray 800, and FIG. 8C shows the end view of the tray 800. FIG. 5F shows the sectional view of section C-C of FIG. 8A, FIG. 8E shows the sectional view of section D-D of FIG. 8A, and FIG. 8D shows the sectional view of section E-E of FIG. 8E.

The side view of FIG. 8B shows the left side wall 802, with opening 820 to accommodate the pivot pin which secures the top arm to the frame 800. The groove 870 is used as a measuring device, also referred to as the distraction gauge, by including a scale which indicates the position of the step pin. Though only the left distraction gauge 870 is shown in FIG. 8B, an identical gauge is present on the right side for measuring the distraction of the right top arm 804. Thus, the instrument frame has an independent distraction gauge for each top arm, which is used to measure the vertebrae distraction. Opening 844 accommodates the lift pin which secures the lift arm to the instrument frame. Lip 880 serves to contact a similar lip on the top arm and prevents the top arm from rising past the lip. The end view of FIG. 8C shows left opening 836 which accommodates the left hex nut and right opening 838, which accommodates the right hex nut.

Figure 8F:
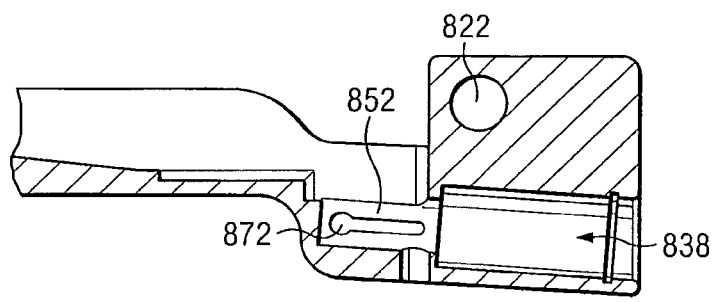

FIG. 8F shows the sectional view of part of the right side wall of section C-C of FIG. 8A, showing the cylindrical opening 852, which accommodates the pull pin, and cylindrical opening 838, which accommodates the pull nut. Right opening 822 for the right pivot pin is also shown in FIG. 8F.

FIG. 8A shows the left cylindrical opening 850 for accommodating the left pull pin and the left draw arm which is coupled to the left pull pin, and the right cylindrical opening 852 for accommodating the right pull pin and the right draw arm which is coupled to the right pull pin. FIG. 8A also shows the left opening 840 for the left lift arm, and the right opening 842 for the right lift arm. FIG. 8E shows the sectional view D-D of FIG. 8D, illustrating the right opening 842 for the right draw arm and hole 846 for the right lift pin which secures the right lift arm to the instrument frame. FIG. 8F shows a sectional view of section E-E of FIG. 8E, showing another view of the left hole 840 for the left lift pin and the right hole 842 for the right lift pin.

FIG. 8D shows another feature of the present disclosure. The bottom of the tray 846 is located below the position of the stationary fingers 848. This provides an access area for the surgeon to remove the damaged disc after distraction of the vertebrae and prior to the insertion of the graft. In one preferred embodiment, the graft tray bottom is about 2 mm below the contact area of the stationary fingers.

FIG. 9A shows the side view of the draw arm 900. The draw arm is coupled to the pull pin through the step pin by opening 904 at the proximal end of the draw arm. The draw arm is coupled to the lift arm through the pivot pin by opening 902 at the distal end of the draw arm. As can be seen in FIG. 9A, the proximal end of the draw arm has a short protrusion 910. The protrusion 910 allows the draw arm to be coupled to the pull pin, which located lower in the instrument frame, and helps transfer the transverse motion of the pull pin, which is in the direction of the main axis of the pull pin and the instrument frame, into a motion that rotates the lift arm (see FIG. 4A for the position of the draw arm in the instrument frame). FIG. 9C shows the top view of the draw arm. The thin draw arm fits on top of the side wall of the instrument frame (see sidewalls 802 and 804 in FIG. 5A). FIG. 9B shows the end view of the lift arm.

FIG. 10A shows the lift arm in detail. The lift arm has two openings. Opening 1002 accommodates the lift pin, which secures the lift arm to the instrument frame. Opening 1004 accommodates the pivot pin, which couples the lift arm to the draw arm. The lift arm rotates around the lift pin as it lifts in a rotational motion. The curved upper surface 1006 of the lift arm contacts a similarly curved bottom surface of the top arm and elevates the top arm. FIG. 10B shows the side view of the lift arm, illustrating how the thin lift arm fits into the openings 840 or 842 shown in FIG. 8D.

Figure 11C:
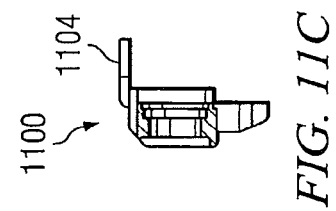
FIGS. 11A-11C show several views of one embodiment of a top arm according to the present disclosure.
Figure 11A:
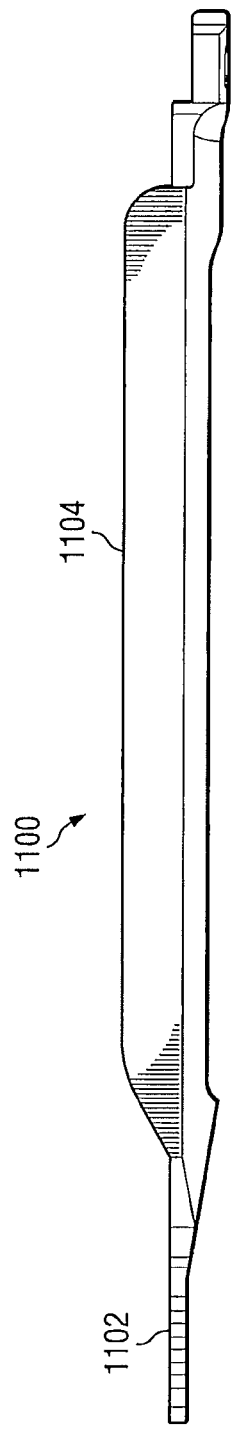
Figure 11B:
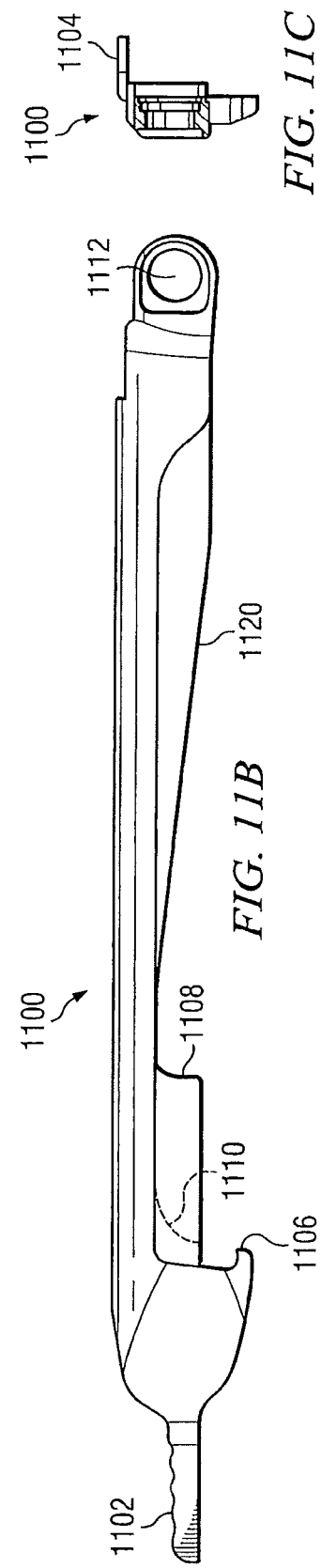

FIG. 11A shows the top view of the top arm 1100 (in this case, the left top arm is shown). The flange 1104 can be seen in this figure, which serves to protect the access pathway formed by the base and side walls of the instrument frame. The distal end of the top arm ends in the adjustable finger 1102, which can be serrated for a more secure contact area. The flange 1104 can also be seen in the end view of FIG. 11C. FIG. 11B shows the side view, which illustrates the opening 1112, which couples the top arm to the instrument frame through a pivot pin. The top arm has two lips 1108 which descend down to cover the lift arm. The lift arm fits between these two lips and the curved surface of the lift arm (item 1006 in FIG. 10A) contacts the curved surface 1110 of the top arm. Lip 1106 serves to prevent the top arm from being elevated past a maximum distance by contacting a similar lip on the instrument frame (item 880 in FIG. 8B) and limits the maximum separation distance of the movable finger 1102 of the top arm and the stationary finger of the instrument frame. In addition, the top arm has an internal shield 1120. When the top arm is activated and thus in an elevated position, the internal shield 1120 spans the opening between the instrument frame and the top of the top arm. This protects the sides of the instrument and helps to maintain a clear passageway for graft insertion.

In a preferred embodiment, the passageway of the instrument is 28 mm wide, 20 mm high, and 240 mm long. In another preferred embodiment, the passageway of the instrument is 25 mm wide, 20 mm high, and 240 mm long. The dimensions of the passageway are determined by the size of the vertebrae of the patient and by the type of vertebrae being distracted. In one preferred embodiment, the size of each of the serrated fingers is 5 mm high, tapered to 4.5 mm high at the tip, and 2.5 mm thick.

Figure 12A:
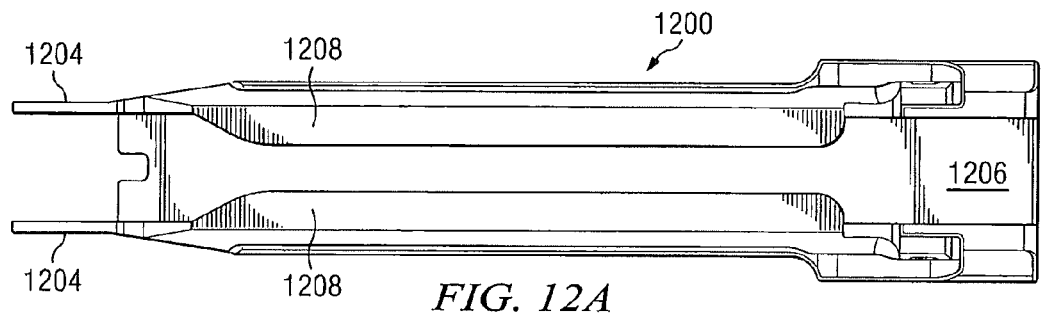
FIGS. 12A-12B show two views of another embodiment of a surgical device according to the present disclosure.
Figure 12B:
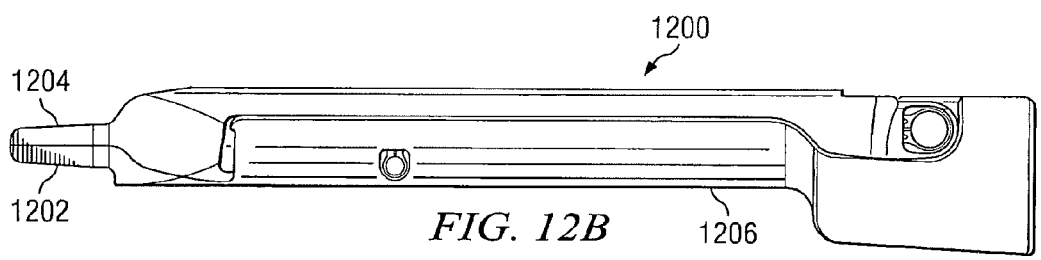

FIGS. 12A and 12B show a second embodiment according to the present disclosure and illustrate the complete instrument 1200. FIG. 12A shows the top view of instrument 1200 and FIG. 12B shows the side view of instrument 1200. In this embodiment, stationary fingers 1202 of the instrument frame 1206, and the movable fingers 1204 of the top arms 1208 are not serrated. In addition, there is no measurement device and therefore no groove in the instrument frame for the movement of the step pin, the step pin not extending into the side wall of the instrument frame.

This second embodiment of the present disclosure is useful in applications when it is desirable to have a smoother outer surface of the instrument. Having smooth fingers without the serration and omitting the groove and extended step pin which form a measurement device provide for such a smoother outer surface and lessen the chance of snagging, pinching, or otherwise damaging delicate soft tissues while the instrument is being put into position.

Figure 13A:
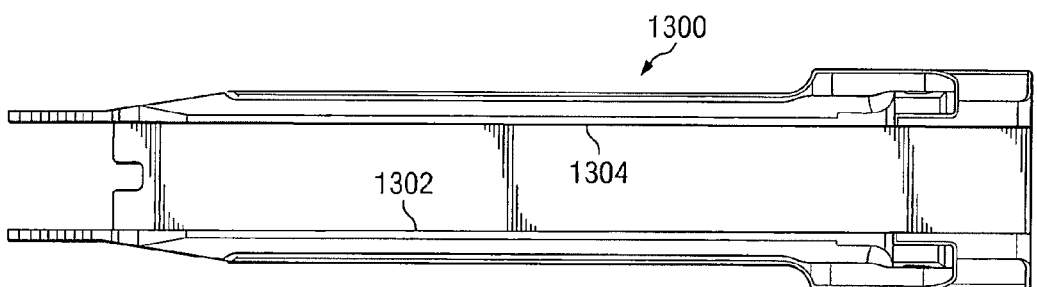
Figure 13B:
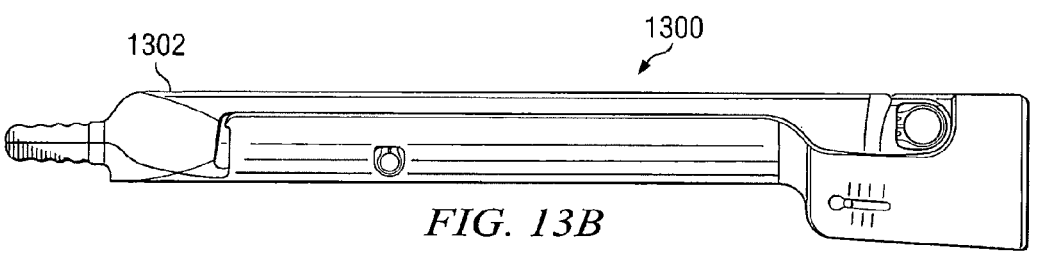

FIGS. 13A, 13B, and 13C show various views of a third embodiment of the present disclosure and illustrate the complete instrument 1300. As shown in FIG. 13A, which shows the top view of the instrument, neither the left top arm 1302 nor the right top arm 1304 have a flange. FIG. 13C shows an end view, showing that the longitudinal place window 1310 is not covered on top with a flange and thus remains larger along the whole length of the instrument.

Another embodiment of the present disclosure may be useful in applications where the access path for the implantation graft needs to remain more open and visible. This is useful when the graft is larger, has an irregular shape, or is more delicate, and the movement of the graft through the access path 1310 of FIG. 13C needs more space.

In some embodiments, the flanges of the top arms may extend all the way across and completely cover the longitudinal place window. In the embodiment show in FIGS. 13A-13C, the clear passageway is completely protected from the top.

Figure 14A:
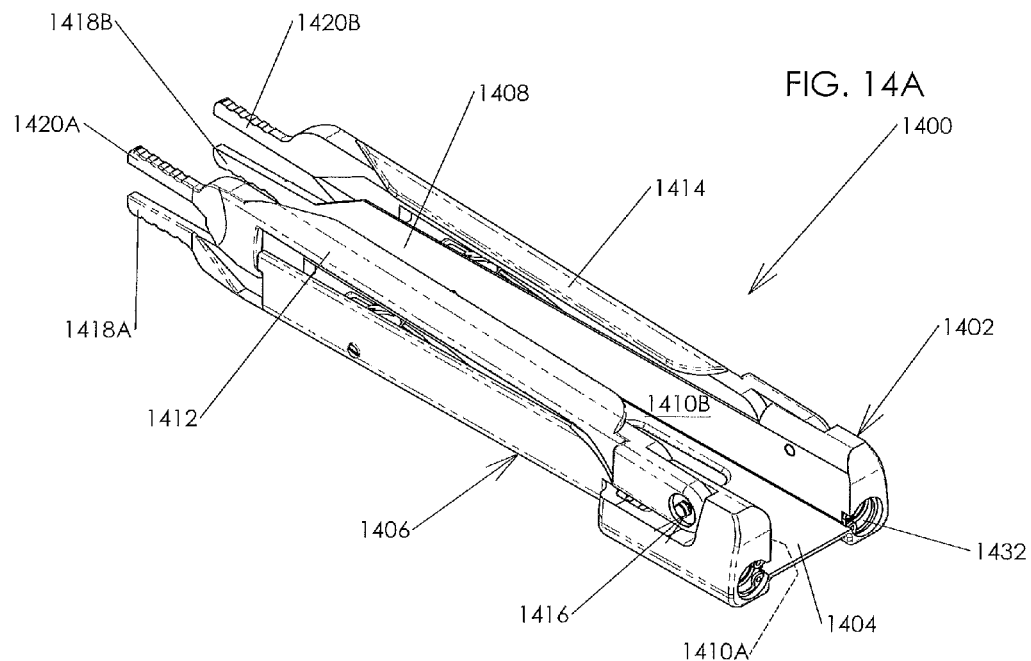
FIG. 14A is a perspective view of another embodiment of a surgical instrument according to the present disclosure.

Referring now to FIG. 14A, there is shown a perspective view of a surgical instrument 1400, comprising yet another embodiment of a surgical instrument according to the present disclosure. Certain aspects of instrument 1400 are similar to the embodiments shown in FIGS. 2A through 13C and described hereinabove, but certain features will now be described in more detail. Instrument 1400 comprises a base 1402 having a proximal and distal end. The base 1402 comprises a tray 1404 having a left base member 1406 and a right base member 1408 on opposing sides thereof. In some embodiments the left base member 1406 and right base member 1408 may comprise interior walls 1410A and 1410B which couple with the tray for substantially enclosing the tray, which enables a surgeon to insert and remove tissue, grafts, and other objects without catching and or tearing on any inner surfaces or mechanisms of the instrument.

A left adjustable top arm 1412 is moveably coupled near the proximal end of the left base member 1406 and similarly, a right adjustable top arm 1414 is moveably coupled near the proximal end of the right base member 1408. Top arms 1412 and 1414 may be pivotably coupled in some embodiments such that the arm pivots angularly upward and downward from a coupling joint such as joint 1416. At the distal ends of the left member 1406 and left right member 1408 are coupled a left bottom finger 1418A and right bottom finger 1418B, respectively. In some embodiments, the bottom fingers 1418A and 1418B may be formed into the distal end of the base members such that the finger and members may comprise one continuous integral member. In some embodiments, the bottom fingers 1418A and 1418B may be substantially stationary such that their position may not change relative to adjacent body tissue and/or vertebrae once the instrument 1400 is inserted into a surgical field. Opposing the bottom fingers are a left top adjustable finger 1420A and right top adjustable finger 1420B coupled to the distal ends of the left and right top arms 1412 and 1414, respectively. Top fingers 1420A and 1420B may also be formed onto the distal ends of the top arms such that the top fingers and top arms may each comprise a continuous integral arm. The top fingers 1420A and 1420B may be separately and independently adjustable relative to the position of the bottom fingers 1418A and 1418B for various separation distances. The bottom fingers 1418A and 1418B, and top fingers 1420A and 1420B are similar in function and structure to fingers 206, 216, 208, and 218 shown in FIGS. 2A and 2B and described hereinabove. The left fingers 1418A and 1420A may be displaced individually to a different separation distance than the right fingers 1418B and 1420B, and vice versa, similar to the displacement discussed hereinabove in conjunction with FIGS. 2A and 2B. The displacement of the adjustable fingers will be described in more detail hereinafter.

Figure 14B:
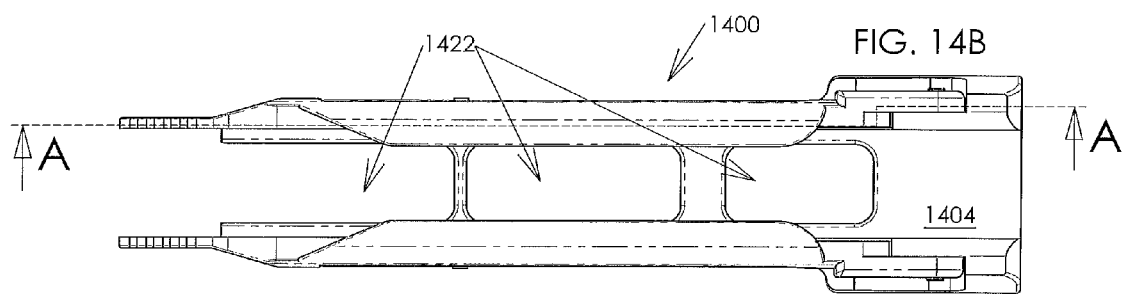
FIG. 14B is a top view of the surgical instrument shown in FIG. 14A.

Referring now to FIG. 14B, in some embodiments, the tray 1404 may comprise one or more openings 1422 therein. Openings 1422 in tray 1404 enable greater visibility and alternative accessibility as needed for various configurations and procedures.

Figure 14C:
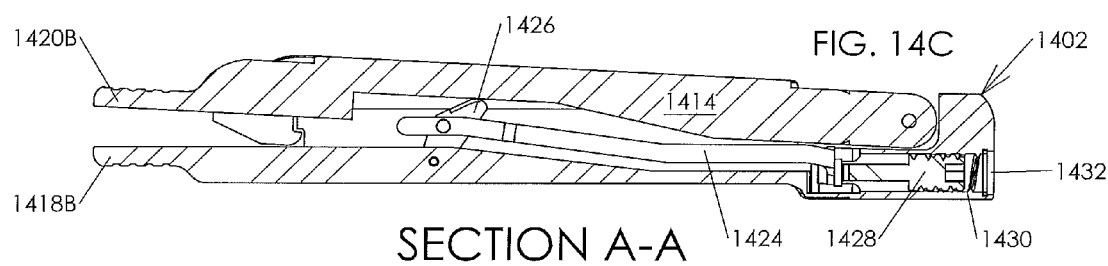
FIG. 14C is a side sectional view of the surgical instrument shown in FIGS. 14A and 14B.

Referring now to FIG. 14C, there is shown a side sectional view of instrument 1400 of the right side of instrument 1400. The right adjustable top arm 1414 is moveably coupled above right base member 1408 near the proximal end thereof. Situated between the base member 1408 and top arm 1414 is a lifting arm 1424 having a cam 1426 fastened thereon. The lifting arm is pushed forward by a push pin 1428 located beneath the proximal end of the top arm 1414 near the proximal end of the base 1402. Push pin 1428 may be threaded and rotate within a threaded cavity 1430 near the proximal end of base member 1408. The push pin 1428 may have a similar hexagonal fitting on one end such that the push pin may be activated and rotated by a hex drive, such as hex drive 202 or similar engagement tool, inserted through opening 1432 in the proximal end of the base 1402. The hex drive engages the push pin 1428, thereby pushing push pin 1428 forward, thereby pushing lifting arm 1424 forward along a linear axis along base member 1408 and towards the distal end of base member 1408. As the lifting arm 1424 is pushed forward, the cam 1426 rotates and engages top arm 1414. As the distal end of the top arm 1414 lifts upwards, the top finger 1420B on the distal end is displaces so as to increase a separation distance between the bottom finger 1418B and top finger 1420B. Although FIG. 14C is illustrated and describe in relation to components comprising the right side of instrument 1400, it is understood that the components comprising the left side of the instrument are similar in construction and function.

Figure 14D:
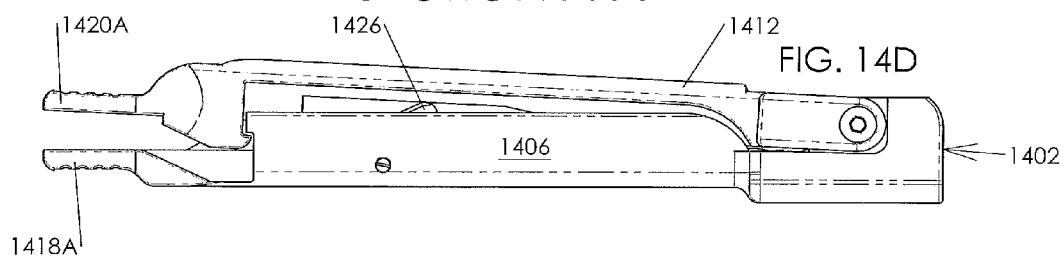
FIG. 14D is a side view of the surgical instrument shown in FIG. 14A through 14C having top arms and adjustable fingers displaced according to the present disclosure.

Referring now to FIG. 14D, there is shown a side view showing the instrument 1400 having top arm 1412 and top finger 1420A displaced. While not shown, the right base member 1408 and top arm 1414 may be engaged similarly and the right top finger 1420B displaced similarly. Accordingly, the left top arm 1420A and right top arm 1420B may be adjusted separately and independently of each other such that the instrument 1400 may be used in a variety of configurations as needed for various procedures, with a separation distance between the left fingers 1418A and 1420A different and independent of a separation distance between the right fingers 1418B and 1420B. Instrument 1400 may utilize hex drive 202 and measurement tool 230, such as a distraction gauge, to finely tune the separation distance of the fingers and achieve a desired distraction distance on each side. Such a desired distraction distance can be determined diagnostically before surgery. Upon completion of a procedure, the hex drive 220 may be used to engage the push pin 1428 in a reverse direction, thereby disengaging the lifting arm 1426 and cam 1428 to lower the top arm 1414 and decrease the separation distance between fingers 1418B and 1420B.

Referring now to FIGS. 15A and 15B there is shown another embodiment of a surgical instrument according to the present disclosure. Instrument 1500 comprises similar components and construction to instrument 1400, but comprises additional features. Instrument 1500 and comprises a base 1502 having a length L. The base comprises tray 1504 having openings thereabove for receiving a removable sleeve 1506 therein.

Referring now to FIG. 15B, sleeve 1506 comprises a planar surface without any openings thereon such that insert may be inserted if needed to substantially enclose tray 1502. Likewise, insert 1506 may be removed if openings in the tray 1502 are needed for increased accessibility and/or visibility during a procedure. In some embodiments, sleeve 1506 may have a length greater than the length L of base 1502, for a greater extraction field, or when additional planar surface area behind the proximal end of the instrument may be required.

Referring now to FIG. 15C, there is shown a partial view of the proximal end of base 1502. Above tray 1504 and at a bottom surface of left inner side wall 1510B there is an opening 1512 which extends the length L of the base for receiving tray 1506 therein. (Although not shown, there is a similar opening near opposing right inner side wall 1510A.)

Referring now to FIG. 15D, there is shown a partial view of the proximal end of base 1502 having sleeve 1506 inserted therein. In one embodiment, the sleeve 1506 is retained in place within the openings 1512 by a tension fit. However, in some embodiments, fasteners or temporary adhesives may be utilized if needed to maintain the sleeve 1506 in place.

The present disclosure also relates to a method of manufacturing embodiments of a surgical device as described hereinabove and shown in FIGS. 2A, 2B, 14A, and 15A, inter alia. Accordingly, some embodiments of a surgical instrument according to the present disclosure may comprise biocompatible metals, such as, e.g., stainless steel, cobalt containing metals, or titanium and various other metals used for fabrication of surgical instruments such that the instrument may be easily cleaned, repaired, and reusable, and such that the instrument may be autoclaved before each use for sterilization prior to surgery. One example of a biocompatible steel is type 316L, which contains a significant amount of nickel, which helps in resisting the corrosion resistance of chloride ions present in the human body.

Various other components of the surgical instrument may also comprise or be lined with metals and non-metal materials, such as, e.g., Co—Cr compound, which are known by those skilled in the art for having smooth surfaces; and polyetheretherketones (PEEK), which are well known in the art for their chemical resistance, prevent galling, and achieve a smooth operation. In certain components, the use of dissimilar metals may be advantageous for improved functionality, such as, e.g., the internal threads of the pull nut 214 and similarly push pin 1426 may be made of dissimilar material to the components comprising the base, and in particular the cavity within the proximal end thereof, for smooth activation.

Although the present disclosure has been described in detail, those skilled in the pertinent art should understand that they can make various changes, substitutions and alterations herein without departing from the spirit and scope of the disclosure in its broadest form.

What is claimed is:

1. A surgical instrument comprising:
    a base having a tray, a first member and a second member, said base, tray, first member and second member each comprising a proximal and distal end and wherein said tray, first member, and second member define a passageway;
    a first top arm coupled near the proximal end of the base;
    a second top arm coupled near the proximal end of the base;
    at least one bottom finger coupled to the distal end of the first member;
    at least one top finger coupled to the distal end of the first top arm;
    at least a first lifting arm located between the first member and the first top arm, said lifting arm comprising a cam for engaging the first top arm; and
    at least one adjustment member positioned near the proximal end of the first member, wherein rotation of said adjustment member engages a proximal end of the at least one lifting arm for moving said lifting arm between said first member and first top arm;
    wherein as the lifting arm moves towards the distal end of the first member, the cam engages and lifts the first top arm thereby displacing the first top finger to a separation distance from the bottom finger.

2. The surgical instrument according to claim 1, further comprising:
    a second bottom finger coupled to the distal end of the second member;
    a second top finger coupled to the distal end of the second top arm;
    a second lifting arm located between the second member and the second top arm, said second lifting arm comprising a cam for engaging the second top arm; and
    a second adjustment member positioned near the proximal end of the second member, wherein rotation of said second adjustment member engages a proximal end of the second lifting arm for moving said second lifting arm between the second member and second top arm;
    wherein as the second lifting arm moves towards the distal end of the second member, the cam engages and lifts the second top arm thereby displacing the second top finger to a separation distance from the second bottom finger.

3. The surgical instrument according to claim 1, wherein the adjustment member is positioned within a cavity and comprises a threaded push pin which moves along a linear access within the cavity.

4. The surgical instrument according to claim 1, wherein the first bottom finger and first top finger are serrated.

5. The surgical instrument according to claim 1, wherein the first bottom finger is formed onto the first member as an integral portion of the distal end thereof.

6. The surgical instrument according to claim 1, wherein the first member and second member each comprise an interior wall coupled with the tray.

7. The surgical instrument according to claim 1, wherein the tray comprises at least one aperture therein.

8. The surgical instrument according to claim 1, further comprising a hex drive wrench which is mated to fit with the adjustment member.

9. The surgical instrument according to claim 1, wherein the surgical instrument comprises a metal selected from the group consisting of stainless steel, a cobalt-chromium alloy, and a titanium alloy.

10. The surgical instrument according to claim 1, wherein the adjustment member comprises a cobalt-chromium alloy and wherein the base comprise a stainless steel.

11. The surgical instrument according to claim 1, wherein the surgical instrument comprises a polyetheretherketone coating.

12. The surgical instrument according to claim 1, wherein the first top arm and the second top arm define a longitudinal place window and wherein the first top arm comprises a first flange that partially covers the longitudinal place window and wherein the second top arm comprises a second flange that partially covers the longitudinal place window.

13. A method for manufacturing a surgical instrument, the method comprising:
  providing a base having a tray, a first member and a second member, said base, tray, first member and second member each comprising a proximal and distal end and wherein said tray, first member, and second member define a passageway;
  providing a first top arm and coupling said first top arm near the proximal end of the base;
  providing a second top arm and coupling said second top arm near the proximal end of the base;
  providing at least one bottom finger and coupling said one bottom finger to the distal end of the first member;
  providing at least one top finger and coupling said one top finger to the distal end of the first top arm;
  providing at least a first lifting arm located between the first member and the first top arm, said lifting arm comprising a cam for engaging the first top arm; and
  providing at least one adjustment member, said adjustment member positioned near the proximal end of the first member, wherein rotation of said adjustment member engages a proximal end of the at least one lifting arm for moving said lifting arm between said first member and first top arm.

14. The method according to claim 13, further comprising:
  providing a second bottom finger and coupling said second bottom finger to the distal end of the second member;
  providing a second top finger, and coupling said second top finger to the distal end of the second top arm;
  providing a second lifting arm located between the second member and the second top arm, said second lifting arm comprising a cam for engaging the second top arm; and
  providing a second adjustment member positioned near the proximal end of the second member, wherein rotation of said second adjustment member engages a proximal end of the second lifting arm for moving said second lifting arm between the second member and second top arm.

15. The method according to claim 14, further comprising a hex drive wrench which is mated to fit with the first and second adjustment members.

16. The method according to claim 13, wherein the first adjustment member is positioned within a cavity and comprises a threaded push pin which moves along a linear access within the cavity.

17. The method according to claim 13, wherein the first bottom finger and first top finger are serrated.

\* \* \* \* \*